United States Patent [19]

Wright

[11] Patent Number: 4,614,802
[45] Date of Patent: Sep. 30, 1986

[54] 6-SUBSTITUTED AMINO-4H-PYRANO(3,2-G)QUINOLINE-2,8-DICARBOXYLIC ACID INTERMEDIATES

[75] Inventor: Robert G. M. Wright, Loughborough, England

[73] Assignee: Fisons plc, Ipswich, England

[21] Appl. No.: 616,920

[22] Filed: Jun. 4, 1984

Related U.S. Application Data

[62] Division of Ser. No. 424,392, Sep. 27, 1982, Pat. No. 4,471,119.

[30] Foreign Application Priority Data

Oct. 10, 1981 [GB] United Kingdom ................ 8130643

[51] Int. Cl.$^4$ .......................................... C07D 491/052
[52] U.S. Cl. ............................................... 546/89
[58] Field of Search ........................................ 546/89

[56] References Cited

U.S. PATENT DOCUMENTS 4,356,181 10/1982 Payling et al. ................ 546/89

FOREIGN PATENT DOCUMENTS 2022078 12/1979 United Kingdom ................ 546/89

OTHER PUBLICATIONS

Chem. Abstracts, vol. 94; 103331d (1981).

Primary Examiner—Henry R. Jiles
Assistant Examiner—Dale A. Bjorkman
Attorney, Agent, or Firm—Marshall, O'Toole, Gerstein, Murray & Bicknell

[57] ABSTRACT

Disclosed are compounds of the formula

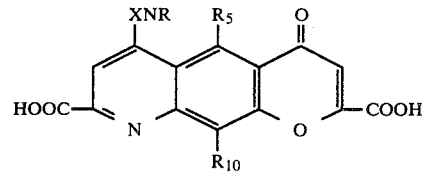

in which
R is hydrogen or alkyl $C_1$ to $C_6$ and $R_5$ and $R_{10}$, which may be the same or different, are hydrogen or alkyl $C_1$ to $C_6$,
X represents a group —$AR_6$,
A is CO or $SO_2$ and $R_6$ is halogen, $C_1$–$C_6$ haloalkyl, $C_1$–$C_6$ alkoxy, $C_6$–$C_9$ aryloxy or phenyl optionally substituted by $C_1$–$C_6$ alkyl, and salts, esters, and amides which are intermediates to anti-allergic compounds.

3 Claims, No Drawings

6-SUBSTITUTED AMINO-4H-PYRANO(3,2-G)QUINOLINE-2,8-DICARBOXYLIC ACID INTERMEDIATES

This is a division of application Ser. No. 424,392, filed Sept. 27, 1982, U.S. Pat. No. 4,471,119.

This invention relates to a novel process.

4-Alkylaminoquinoline derivatives are usually prepared by conversion of the 4-oxo group of a 4-quinolone to a leaving group, followed by replacement of the leaving group by an alkylamine, e.g. British patent application number 2035312A.

However this method is inappropriate when the quinolone starting material bears other functional groups which react with alkylamines, e.g. a 4-oxo-4-H-pyrano-2-carboxy ring.

According to the invention we provide a process for the production of a compound of formula I,

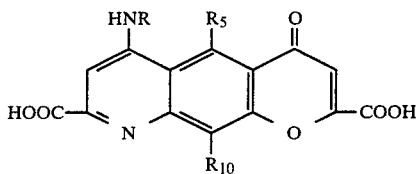

in which
R is hydrogen or alkyl $C_1$ to $C_6$, and $R_5$ and $R_{10}$, which may be the same or different, are each hydrogen or alkyl $C_1$ to $C_6$,
or a pharmaceutically acceptable derivative thereof,
which comprises removal of an activating group from a compound of formula II,

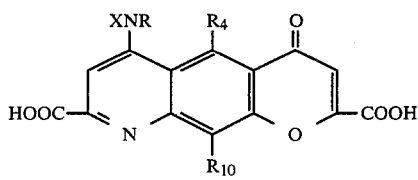

or a suitable derivative thereof,
in which R, $R_5$ and $R_{10}$ are as defined above, and X represents an activating group,
and if desired or necessary converting the resulting compound of formula I to a pharmaceutically acceptable derivative thereof, or vice versa.

The activating group X may be a group —$AR_6$, in which A is CO or $SO_2$ and $R_6$ is halogen e.g. chlorine, haloalkyl, alkoxy $C_1$-$C_6$, e.g. ethoxy, aryloxy $C_6$-$C_9$, e.g. chlorophenoxy, or phenyl optionally substituted by alkyl $C_1$ -$C_6$. More specifically the activating group may be —$COCCl_3$, —$SO_2OR_7$, where $R_7$ is phenyl optionally substituted by halogen, e.g. chlorine; or preferably p-toluenesulphonyl.

The removal of the activating group may be affected by hydrolysis, or by reductive cleavage, e.g. with zinc and acetic acid, or hydrogen and a palladium on charcoal catalyst. The hydrolysis may be effected under basic, e.g. sodium hydroxide, conditions, or using acidic conditions. When the activating group is p-toluenesulphonyl, it is preferably removed using acidic hydrolysis, e.g. using sulphuric acid, or a mixture of acetic and hydrobromic acids. The hydrolysis may be carried out at a temperature of from about 5° to 120° C. The hydrolysis may be carried out in a solvent which is inert under the reaction conditions, for example a $C_1$-$C_6$ alkanol, e.g. ethanol or methanol.

If desired, the removal of the activating group, and the cleavage of suitable derivatives of one or both of the carboxy groups to carboxy groups may be carried out concurrently, for example, using sulphuric acid.

The compounds of formula II are novel and may be made by an entirely novel reaction which has no precedent in the literature.

Thus according to a further feature of the invention we provide a process for the production of a compound of formula II in which R is hydrogen, or a suitable derivative thereof, which comprises reaction of a compound of formula III,

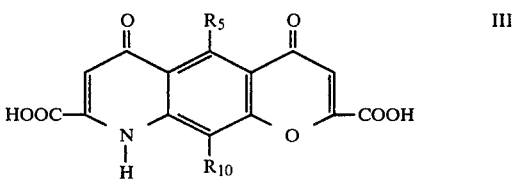

or a suitable derivative thereof,
in which $R_5$ and $R_{10}$ are as defined above, with a compound of formula IV,

$$X-N=C=O \qquad IV$$

in which X is as defined above.

The reaction may be carried out in a solvent which is inert under the reaction conditions, e.g. dichloroethane, dichloromethane or acetonitrile. The reaction may be carried out at a temperature of from about 15° C. to 150° C., e.g. the reflux temperature of the reaction mixture. We prefer to carry out the reaction using from 5 to 30% w/v of the compound of formula III in the solvent and using from about 0.8 to 1.5, and preferably one, equivalent of the compound of formula IV for each equivalent of the compound of formula III.

To produce a compound of formula II, in which R is alkyl, or a suitable derivative thereof, a corresponding compound of formula II, or a suitable derivative thereof, in which R is hydrogen may be alkylated using an alkylating agent, for example dialkyl sulphate, e.g. dimethyl sulphate, alkyl tosylate, e.g. methyl tosylate or preferably an alkyl halide, e.g. methyl iodide, in a solvent which is inert under the reaction conditions, e.g. N-methylpyrrolidone, and in the presence of a proton acceptor, e.g. potassium carbonate.

We prefer the above reactions to be carried out using a derivative, for example a salt, amide or more preferably an ester, of the carboxylic acid groups. Suitable salts include ammonium, alkali metal (e.g. sodium, potassium and lithium) and alkaline earth metal (e.g. calcium or magnesium) salts, and salts with suitable organic bases, e.g. salts with lower alkylamines, such as methylamine or ethylamine. Suitable esters include simple lower alkyl esters, e.g. the ethyl ester, esters derived from alcohols containing basic groups, e.g. di-lower alkyl amino substituted alkanols such as the 2-(diethylamino)-ethyl ester, and acyloxy alkyl esters, e.g. a lower acyloxy-lower alkyl ester such as the pivaloyloxymethyl ester. The suitable amides may be, for example, unsubstituted or mono- or di- $C_1$ to $C_6$ alkyl or phenyl amides.

The compounds of formula I and pharmaceutically acceptable derivatives thereof are of known utility as pharmaceuticals, e.g. as anti-allergic compounds.

Pharmaceutically acceptable derivatives of the compounds of formula I include pharmaceutically acceptable salts, esters and amides of the 2- and/or 8-carboxylic acid group. Suitable salts include ammonium, alkali metal (e.g. sodium, potassium and lithium) and alkaline earth metal (e.g. calcium or magnesium) salts, and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, with simple monocyclic nitrogen heterocyclic compound, e.g. piperidine or morpholine, with an amino acid, e.g. lysine, ornithine, arginine, or an N-alkyl, especially an N-methyl derivative of any one thereof, or with an aminosugar, e.g. glucamine, N-methylglucamine or glucosamine. Specifically included are compounds in which only one —COOH group is in salt form. Suitable esters include simple lower alkyl esters, e.g. the ethyl ester, esters derived from alcohols containing basic groups, e.g. di-lower alkyl amino substituted alkanols such as the 2-(diethylamino)-ethyl ester, and acyloxy alkyl esters, e.g. a lower acyloxy-lower alkyl ester such as the pivaloyloxymethyl ester. The pharmaceutically acceptable acid addition salts of the compounds of formula I, e.g. the hydrochloride, the hydrobromide, the oxalate, the maleate or the fumarate salts, are also included. The amides may be, for example, unsubstituted or mono- or di- $C_1$ to $C_6$ alkyl or phenyl amides.

We prefer compounds of formula I in which $R_5$ is hydrogen and $R_{10}$ is $C_1$ to $C_6$ alkyl, specifically propyl.

We particularly prefer compounds of formula I in which R is alkyl $C_1$ to $C_3$, e.g. methyl.

We specifically prefer the compound of formula I in which R is methyl, $R_5$ is hydrogen and $R_{10}$ is propyl.

The compounds of formula I, and the intermediates therefor, may be isolated from their reaction mixtures using conventional techniques which are known per se.

The invention is illustrated, but in no way limited by the following Examples.

EXAMPLE 1

Diethyl 6-methylamino-4-oxo-10-propyl-4H-pyrano[3,2-g]quinoline-2,8-dicarboxylate (a) Ethyl 8-methoxycarbonyl-4-oxo-10-propyl-6(4-toluenesulphonamido)-4H-pyrano[3,2-g]quinoline-2-carboxylate Ethyl 6,9-dihydro-4,6-dioxo-8-methoxycarbonyl-10-propyl-4H-pyrano[3,2-g]quinoline-2-carboxylate (38.5 g, 0.1 mol) was suspended in dichloroethane (200 ml) and 4-toluene-sulphonyl isocyanate (15.1 ml; 0.1 mol) added at room temperature. The whole was then refluxed for 16 hours, allowed to cool, and filtered, to give the sub-title compound as brilliant yellow cubes, 44.0 g (82%), m.p. 219° C.

(b) Ethyl 8-methoxycarbonyl-4-oxo-10-propyl-6(N-methyl-4-toluenesulphonamido)-4H-pyrano[3,2-g]quinoline-2-carboxylate The product of step (a) (5.38 g, 0.01 mol) was suspended in N-methyl pyrrolidone (40 ml), and potassium carbonate (1.38 g, 0.01 mol) added, to give on stirring at room temperature for five minutes a deep red solution. Methyl iodide (2 ml) was then added, and the whole warmed to 40° C., and stirring continued for one hour. The solution was poured into water (150 ml), to give the sub-title compound on filtration, as a white powder, 5.44 g, (98.6%), m.p. 173°–174° C.

(c) Diethyl 6-methylamino-4-oxo-10-propyl-4H-pyrano-[3,2-g]quinoline-2,8-dicarboxylic acid The product of step (b) (5.52 g, 0.01 mol) was dissolved in concentrated sulphuric acid (98%, 5 ml) and warmed at 50° C. for one hour with vigorous stirring. The whole was then slowly poured into ethanol (50 ml), and refluxed for 3 hours. This solution was then added slowly to water (35 ml) containing aqueous ammonia solution (0.88 specific gravity, 15 ml), to give a thick orange precipitate. Filtration gave the desired product, 3.16 g (76%) as a pale orange powder, mp 235°–237° C.

EXAMPLE 2

Ethyl 8-methoxycarbonyl-6-methylamino-4-oxo-10-propyl-4H-pyrano[3,2-g]-quinoline-2-carboxylate The product of step 1(b) (10 g, 0.018 mol) was dissolved in sulphuric acid (98%, 20 ml) at room temperature. During dissolution the internal temperature rose to 40° C., and the solution became deep red. The solution was then stirred for 2 hours, during which time the temperature of the reaction fell to 25° C. The acidic solution was added to ice/water (200 ml) over two minutes, the temperature being held below 10° C. The aqueous solution formed was red-brown solution. After about 5 minutes from the beginning of the addition a yellow precipitate formed. Aqueous ammonia solution (0.88 specific gravity) was added to the stirred yellow slurry, and as the pH rose, the slurry turned orange. Ammonia addition was ceased when the pH of the slurry reached 9. The orange precipitate was filtered off, washed with water (50 ml), dried in vacuo at 70° C. to give the title compound, 6.8 g (95%), which high performance liquid chromatography (HPLC) showed to be 93.5% pure. N.m.r., CDCL$_3$, δ: 8.6, s, 1H; 7.1, s, 1H; 7.05, s, 1H, 5.85, broad q, 1H; 4.45, q, 2H; 3.95, s, 3H; 3.75, t, 2H; 3.15, d, 2H; 1.8, m, 2H; 1.5, b, 3H; 1.05, t, 3H.

EXAMPLE 3

6-Methylamino-4-oxo-10-propyl-4H-pyrano[3,2-g]-quinoline-2,8-dicarboxylic acid

The product of step 1(b) (5 g, 0.009 mol) was dissolved in sulphuric acid (98%, 50 ml) and then heated to 100° C. Heating at 100° C. was maintained for 18 hours, then the solution was cooled to 30° C., and added to ice/water (500 ml), to give a yellow precipitate. The precipitate was isolated by filtration, washed with water (100 ml), and dried in vacuo at 60° C. over 16 hours to give 3.0 g (93%) of the title compound. HPLC of the product, eluting with ammonium acetate/methanol established identity of the compound using the known disodium salt of the title compound as reference, and showed a purity of 95%.

EXAMPLE 4

Ethyl 6-amino-8-methoxycarbonyl-4-oxo-10-propyl-4H-pyrano[3,2-g] quinoline-2 carboxylate

(a) Ethyl 6(4-chlorophenoxysulphamido)-8-methoxycarbonyl-4-oxo-10-propyl-4H-pyrano[3,2-g]quinoline-2-carboxylate 4Chlorophenoxysulphonylisocyanate (2.0 ml, 2.90 g) was added to a suspension of ethyl 6,9-dihydro-4,6-dioxo-8-methoxycarbonyl-10-propyl-4H-pyrano[3,2-g]quinoline-2-carboxylate (3.85 g, 10 mmol) in dichloroethane (20 ml), and then refluxed for 4 hours. Removal of the solvent by distillation in vacuo, and trituration with ether gave the desired product, 5.05 g (88%), as yellow crystals.

Microanalysis: $C_{26}H_{23}ClN_2O_9S$: calculated C: 54.31%, H: 4.00%, N: 4.87%. found C: 53.96%, H: 3.99%, N: 4.79%.

(b) Ethyl 6-amino-8-methoxycarbonyl-4-oxo-10-propyl-4H-pyrano[3,2-g]quinoline-2 carboxylate The product of step (a) (1.0 g) was dissolved in ethanolic hydrogen chloride (50 ml), and refluxed for 0.2 hours. The pale yellow solution was poured into aqueous ammonia solution (100 ml), cooled to 0° C., and the orange precipitate obtained, filtered, washed with water, to give the desired product as an orange powder, 0.55 g, mp 267°–270° C. (decomposes).

EXAMPLE 5

Ethyl 6-amino-8-methoxycarbonyl-4-oxo-10-propyl-4H-pyrano[3,2-g]-quinoline-2-carboxylate

(a) Ethyl 8-methoxycarbonyl-4-oxo-10-propyl-6-trichloroacetamido-4H-pyrano[3,2-g)quinoline-2-carboxylate Trichloroacetyl isocyanate (1.18 ml, 10 mmol) was added to a solution of ethyl 6,9-dihydro-4,6-dioxo-8-methoxycarbonyl-10-propyl-4H-pyrano[3,2-g]quinoline-2-carboxylate (3.85 g, 10 mmol) in dichloromethane (20 ml) at room temperature. The solution was then agitated gently for 24 hours at room temperature and then the solvent removed by distillation in vacuo. Trituration of the resulting solid with ether gave the sub-title compound as yellow cubes, 4.25 g (80%), mp 167°–169° C.

(b) Ethyl 6-amino-8-methoxycarbonyl-4-oxo-10-propyl-4H-pyrano [3,2-g]-quinoline-2-carboxylate The product of step (a) (1.0 g) was dissolved in concentrated sulphuric acid (1 ml) and stirred vigorously for 0.5 hours. The deep rep solution was then poured into iced aqueous ammonia solution (100 ml), and the precipitate filtered to give the title compound, 0.5 g, as an orange powder, mp 265°–270° C. (decomposes).

EXAMPLE 6

Ethyl 6-amino-8-methoxycarbonyl-4-oxo-10-propyl-4H-pyrano[3,2-g]quinoline-2-carboxylate 4-Chlorophenoxysulphonylisocyanate (0.2 ml, 290 mg) was added to a suspension of ethyl 6,9-dihydro-4,6-dioxo-8-methoxycarbonyl-10-propyl-4H-pyrano[3,2-g]quinoline-2-carboxylate (385 mg, 1 mmol) in acetonitrile (5 ml), and then refluxed for 0.5 h. The solution was allowed to cool, ethanolic hydrogen chloride solution (2 ml) was added, and after 5 minutes the pale yellow solution was poured into aqueous ammonial solution (0.88 specific gravity, 5 ml) at 5° C., to give a thick orange precipitate. Filtration and washing with ethanol (10 ml) gave the title compound, 320 mg (83%) as an orange powder, mp 268°–270° C. (decomposes).

I claim:

1. A compound of the formula

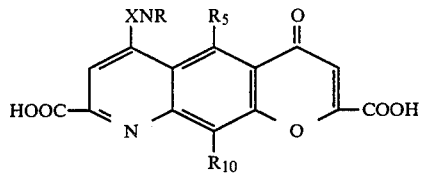

in which
R is hydrogen or alkyl $C_1$ to $C_6$ and $R_5$ and $R_{10}$, which may be the same or different are hydrogen or alkyl $C_1$ to $C_6$, X represents a group —$AR_6$, A is CO or $SO_2$ and $R_6$ is halogen, haloalkyl $C_1$ to $C_6$, alkoxy $C_1$ to $C_6$, phenoxy optionally substituted by halogen or phenyl optionally substituted by alkyl $C_1$ to $C_6$, or a salt, ester or amide thereof.

2. A compound according to claim 1 wherein X is 4-toluenesulphonyl.

3. A compound according to claim 1, wherein $R_5$ represents hydrogen and $R_{10}$ represents propyl.

* * * * *